(12) United States Patent
Zollinger et al.

(10) Patent No.: US 6,558,677 B2
(45) Date of Patent: *May 6, 2003

(54) VACCINE AGAINST GRAM NEGATIVE BACTERIA

(76) Inventors: Wendell D. Zollinger, 14400 Morton Hall Rd., Silver Spring, MD (US) 20906; David R. Shoemaker, 3433 Gateshead Manor Way, Apt. 301, Silver Spring, MD (US) 20904; Agnes G. Saunders, 2406 Ladymeade Dr., Silver Spring, MD (US) 20906; Brenda L. Brandt, 20006 Spur Hill, Gaithersburg, MD (US) 20879

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/749,592

(22) Filed: Nov. 15, 1996

(65) Prior Publication Data

US 2003/0059444 A1 Mar. 27, 2003

Related U.S. Application Data

(60) Provisional application No. 60/028,542, filed on Oct. 15, 1996.

(51) Int. Cl.[7] .................. A61K 39/02; A61K 39/095
(52) U.S. Cl. .................. 424/234.1; 424/249.1; 424/250.1
(58) Field of Search .................. 424/234.1, 249.1, 424/250.1

(56) References Cited

U.S. PATENT DOCUMENTS 4,601,903 A * 7/1986 Frasch
4,707,543 A * 11/1987 Zollinger et al.
5,552,146 A * 9/1996 Hansen et al.
6,180,111 B1 * 1/2001 Stein et al.

FOREIGN PATENT DOCUMENTS

EP 301992 * 2/1989
WO 9006696 * 6/1990

OTHER PUBLICATIONS

Zollinger et al. Injection and Immunity 6(5): 835–851, 1972.*
Zollinger et al. Infection and Immunity 10 (5) : 975–984, 1974.*
Zollinger et al. Infection and Immunity 18 : 424–433, 1977.*
Zollinger et al. Journal of Clinical Investigation 63: 836–848, 1979.*
Frasch et al. J. Exp. Med 140:87–104, 1974.*
Milagres et al. FEMS 13(1): 9–17, 1996.*
Meyer Naess et al. Journal of Immunological Methods 196 (1): 41–49, 1996.*
Rosenquist et al. Infection and Immunity 63(12): 4642–4652, 1995 (Dec.).*
Peppler et al, Infection and Immunity 37(1):264–270, 1982.*
Van der Ley et al. Vaccine 13(4):401–407, 1995.*
Claassen et al. Vaccine 14(10): 1001–1008, 1996.*
Verheul et al. Infection and Immunity 61(1): 187–196, 1993.*
Van der Ley et al. Infection and Immunity 59 (9): 2963–2971, 1991.*
Frosch et al (Molecular Microbiology vol. 4(7) pp. 1215–1218), 1990.*
Hammerschmidt et al (Molecular Biology vol. 20(6) pp. 1211–1220), 1996.*
Devoe et al. Journal of Experimental Medicine 138: 1156–1167, 1973.*
Levi et al. Vaccine 13(14): 1353–1359, 1995 (Oct.).*
Lowell et al. Gastroenterology 110(4 Suppl.): #A965 (Apr. 1996).*
Fredricksen et al. Proceedings of the report meeting on Sep. 12–13, 1991 at NIPH, Oslow, Norway, NIPH Annals 14(2):67–80, 1991 (Dec.*

* cited by examiner

*Primary Examiner*—Mark Navarro (57) ABSTRACT

A mucosal vaccine for Neisseria based on native outer membrane vesicles (NOMV) prepared from genetically engineered vaccine strain and unexposed to detergents is described. Methods for extending this vaccine approach to other Gram negative bacteria are also decribed.

17 Claims, 9 Drawing Sheets

Figure 1. Bactericidal Antibody Response of Rabbits
Vaccinated Intranasally with Meningococcal NOMV Vaccines Figure 2. IgA Antibody to NOMV in Nasal Washes of Rabbits
Vaccinated Intranasally with NOMV Vaccines Figure 3. Anti-LOS Antibody Response by ELISA of Rabbits Vaccinated Intranasally with NOMV Vaccines Figure 4. Negative stain electron micrograph of NOMV Lot #0123. Magnification about 77,000 X Figure 5. Polyacrylamide gel electrophoresis of NOMV Lot #0123 Stained with Coomassie Blue. The asterisks indicate the proteins that were induced by iron starvation.

Figure 6. Bactericidal Antibody Response of Mice to Intranasal Vaccination with NOMV Lot #0123

Figure 7. Bactericidal Antibody Response of Mice to Intraperitoneal Vaccination with NOMV Lot #0123

Figure 8. Serum IgG Antibody Response of Mice to Intraperitoneal Vaccination with NOMV Lot #0123

Figure 9. Serum IgG Antibody Response of Mice to Intraperitoneal Vaccination with NOMV Lot #0123

Figure 10. Serum IgA Antibody Response of Mice to Intranasal Vaccination with NOMV Lot #0123

Figure 11. Serum IgA Antibody Response of Mice to Intraperitoneal Vaccination with NOMV Lot #0123

Figure 12. Coomassie Blue stain of sodium dodecyl sulfate polyacrylamide gel electrophoresis of NOMV purified by different methods Lanes 1 and 5: molecular weight standards
Lane 2: Ultracentrifugation method, 3 cycles
Lane 3: DEAE/Microfiltration method
Lane 4: DEAE/Ultrafiltration method Figure 13. Coomassie Blue stained sodium dodecyl sulfate polyacrylamide gel of NOMV extracted from E. coli lpp(-), ompA(-) double mutant.

VACCINE AGAINST GRAM NEGATIVE BACTERIA

This application claims benefit of Provisional Application No. 60/028,542, filed Oct. 15, 1996.

INTRODUCTION

Group B meningococcal disease currently accounts for at least one half of all meningococcal disease in many countries including North and South America, and Europe. The emergence of a new virulent clone of group B *Neisseria meningitidis*, known as ET5, in Norway in the late 70's has since been responsible for prolonged epidemics in Norway, Cuba, Brazil, and Chile. These epidemics have created serious public health problems and led to intensive efforts to develop an effective group B vaccine in several of the affected countries. Recently, an outbreak of group B disease caused by the ET5 clone occured in the U.S. Northwest. This could indicate that the ET5 clone is gaining a foothold in the U.S. and that an increase in the incidence of group B disease in the U.S. may occur in the next few years. The absence of a U.S.-licensed group B vaccine along with the poor performance of the A and C capsular polysaccharide vaccines in children under 18 months have prevented serious consideration of routine childhood vaccination against meningococcal disease. Current efforts to develop conjugate group A and C polysaccharide vaccines by several companies will likely yield A and C vaccines with improved performance in young children and will make routine vaccination of children against meningococcal disease more attractive, particularly if an effective group B vaccine becomes available.

Neisseria, including *Neisseria meningitidis* and *Neisseria gonorrhoeae* have an outer membrane that is rather loosely associated with the rigid cell wall peptidoglycan layer and naturally blebs off during growth of the organism [Zollinger, W.D. et al. (1972) *Infect. Immun.* 6:835–851] (All documents cited herein supra and infra are hereby incorporated by reference thereto.). Vesicles of outer membrane can be obtained from a meningococcal culture supernatant or by extraction from the organism by mild procedures [Zollinger, W. D., ibid.]. These vesicles appear to be representative of intact outer membrane and can be easily obtained in high yield. Although an excellent antigen, the use of these vesicles directly as a vaccine against meningococcal disease has been considered impractical because of the high levels of lipopolysaccharide (a potent endotoxin) associated with them. Typically, the weight ratio of LPS to protein in the outer membrane is about 0.3 to 0.8. For many years, efforts have been made to utilize the outer membrane proteins as a vaccine for group B meningococcal disease by using detergents to remove most of the lipopolysaccharide from the outer membrane. These candidate vaccines have been partially successful (50 to 80% efficacy in field trials), but have failed to induce protective antibody responses in children under the age of four years. Protection induced by these vaccines also seems to be of limited duration. The young children have IgG antibody responses against the outer membrane proteins that equals or exceeds those of older children, but most of the antibodies are not bactericidal or protective.

Therefore, there is a need for a *Neisseria meningitidis* vaccine which produces a lasting, protective immunogenic response capable of protecting an individual against meningococcal disease.

SUMMARY

The present invention fulfills the need described above.

The present invention relates to a vaccine and methods of producing a vaccine or vaccines that can be used to immunize an individual against meningococcal disease, and in the extended application, against other Gram negative infections with bacteria such as Shigella, Brucella, Pseudomonas, *E. coli*, and Haemophilus.

The vaccine of the present invention introduce the outer membrane proteins (OMPs) in their natural phospholipid/lipopolysaccharide (LPS) environment as native outer membrane vesicles (NOMV), and results in an improved functional (bactericidal) antibody response to the outer membrane proteins (OMPs) in animals and should behave similarly in humans and children under the age of 4 years. We have shown that this type of vaccine, which is normally considered to be too toxic for use as a parenteral vaccine, can be safely administered via the intranasal route. Intranasal immunization is ideal for meningococcal vaccines since asymptomatic nasopharyngeal colonization by less pathogenic meningococci and closely related species results in natural immunization of most individuals. The human nasopharynx is the natural habitat of *N. meningitidis* and at any given time approximately 5 to 10% of healthy individuals carry it on their throats.

There are several advantages to using a native outer membrane vesicle as an intranasal vaccine for *N. meningitidis* or other Gram negative infection. NOMV can be prepared easily at relatively low cost so the technology and the product produced by it may be more accessible to underdeveloped countries.

The antigens presented as part of NOMV, including the OMPs and the LPS, are in a completely native configuration and environment as part of intact outer membrane that has not been exposed to detergent. This results in an antibody response that is directed primarily toward epitopes exposed on the surface of the intact bacterium. These antibodies are more likely to be functional than if directed against epitopes that are conformationally altered (by detergent extraction for example), or not fully exposed at the surface of the viable organism. In addition, giving the NOMV vaccine intranasally results in very little reactogenicity or toxicity in spite of relatively high endotoxin content.

The intranasal route of vaccination mimics the natural route of immunization for *N. meningitidis* and, as judged by the results of animal experiments, is expected to induce a mucosal immune response as well as a serum antibody response. Antibodies to antigens such as Opc and Opa proteins and pili may play a more important role in protection at the mucosal surface during the initial phases of pathogenesis than they do in the serum where the organism may have turned off their expression. The nasopharynx is the natural portal of infection for the meningococcus.

In the youngest children who have had little exposure to meningococci, it may be particularly important to prime the immune system with a very native antigen that can induce protective antibodies so that subsequent colonization with meningococci will be effective in boosting protective immunity. In contrast, isolated OMPs given as a vaccine tend to induce a preponderance of antibody that is non-functional in a bactericidal assay.

In particular, the present invention relates to the use of NOMV from a vaccine strain that has been genetically modified in order to produce maximum immunogenicity with least toxicity. More specifically, a vaccine strain of the present invention includes a modified strain which does not synthesize sialic acid (capsule and sialylated LPS) resulting in better interaction of the NOMV with the mucosal surface and producing higher immunogenicity.

Preferably, the vaccine strain is grown under iron limiting conditions to induce the expression of the iron uptake proteins including transferrin and lactoferrin binding proteins resulting in a vaccine that contains additional antigens with known protective potential both by inducing bactericidal antibodies and by inducing antibodies that can block the binding of iron by the organism.

Therefore, it is an object of the present invention to provide a Neisseria vaccine comprising purified native outer membrane vesicles of Neisseria in an amount effective to elicit protective antibodies in an animal to Neisseria; and a pharmaceutically acceptable diluent, carrier, or excipient.

It is another object of the present invention to provide a *Neisseria meningitidis* vaccine comprising purified native outer membrane vesicles of *Neisseria meningitidis* in an amount effective to elicit protective antibodies in an animal to *Neisseria meningitidis*; and a pharmaceutically acceptable diluent, carrier, or excipient It is yet another object of the present invention to provide a *Neisseria meningitidis* Group B vaccine comprising purified native outer membrane vesicles of *Neisseria meningitidis* Group B in an amount effective to elicit protective antibodies in an animal to *Neisseria meningitidis*; and a pharmaceutically acceptable diluent, carrier, or excipient It is another object of the present invention to provide a method of preparing a Neisseria vaccine comprising isolating native outer membrane vesicles from Neisseria.

It is yet another object of the present invention to provide a modified strain of *N. meningitidis* for use in the production of native outer membrane vesicles wherein the modified strain is unable to synthesize sialic acid.

It is further another object of the present invention to provide a modified strain of *N. meningitidis* for use in the production of native outer membrane vesicles wherein the modified strain is unable to synthesize sialic acid and expresses iron uptake proteins.

It is yet a further object of the present invention to provide a method for the production of *N. meningitidis* expressing iron uptake proteins by growing *N. meningitidis* in iron deficient media.

It is a further object of the present invention to provide a strain of *N. meningitidis* 9162 synX(−).

It is another object of the present invention to provide a method for the preparation of native outer membrane vesicles comprising extraction of outer membrane vesicles from cells without exposure to detergent, followed by differential centrifugation, treatment of extract supernatant with ion exchange matrix, and ultrafiltration.

It is still another object of the present invention to provide a method for the preparation of outer membrane vesicles from Gram negative bacteria other than Neisseria for use as a vaccine, the method comprising deleting lpp and ompA genes or their equivalents in the bacteria.

It is yet another object of the present invention to provide a vaccine comprising native outer membrane vesicles of Gram negative bacteria other than Neisseria, produced according to the above methods, in an amount effective to elicit protective antibodies in an animal to the Gram negative bacteria and a pharmaceutically acceptable diluent, carrier, or excipient.

Further objects and advantages of the present invention will be clear from the description that follows.

BRIEF DESCRIPTION OF THE DRAWINGS

FIG. 1. Bactericidal antibody response of rabbits vaccinated intranasally with meningococcal NOMV vaccines. Groups of 4 rabbits were vaccinated intranasally at 0, 4 and 8 weeks with either 9162 NOMV from the encapsulated parent strain, lot # D190894, (group 1) or 9162 synX(−) NOMV, Lot # E110195, (group 2). A control group received only normal saline. Rabbits were bled and nasal washes taken at 0, 14, 28, 42, 56, and 70 days. The encapsulated parent strain 9162 was used as the test strain in the bactericidal test. Values are geometric mean reciprocal titers and the error bars represent 1 standard error of the geometric mean.

DETAILED DESCRIPTION

The present invention relates to a vaccine for Neisseria based on native outer membrane vesicles (NOMV) and to methods for preparing such a vaccine and extending this vaccine approach to the preparation of similar vaccines against other Gram negative bacteria.

More particularly, the vaccine for *Neisseria meningitidis* Group B described in this invention results in an improved functional (bactericidal) antibody response to the outer membrane proteins (OMPs) in animals and is expected to give an improved bactericidal antibody response in humans, including children under the age of 4 years, by presenting the OMPs in their natural phospholipid/lipopolysaccharide (LPS) environment as native outer membrane vesicles (NOMV). This type of vaccine, which is normally considered to be too toxic for use as a parenteral vaccine, can be safely administered via the intranasal route. Intranasal vaccination against *N. meningitidis* infections is expected to be an effective route of vaccination because it mimics the process of natural immunization and will induce secretory antibodies at the mucosal surface that may be able to prevent adhesion and/or invasion at the mucosal surface, in addition to inducing bactericidal antibodies in the serum. This type of vaccine will be simple and inexpensive to manufacture and should therefore be accessible to populations at risk in poor underdeveloped countries.

Native outer membrane vesicles can be prepared from any strain of Nesseria, including *N. meningitidis, N. gonorrhoeae*, and *N. lactamica*, expressing the most desirable antigens and suppressing expression of antigens that may interfere with the desired immune response. Desirable antigens would include for example, antigens that have been shown to induce serum bactericidal antibodies, or antibodies that block uptake of iron and thereby prevent growth, or antibodies that prevent invasion at the mucosal surface. Among these are PorA, PorB, Opc, transferrin and lactoferrin binding proteins, LPS and others that are less well characterized. Because antigenic variation occurs with most of these antigens, it would likely be desirable to cause expression of multiple antigenically different copies of certain proteins such as PorA [Ley PA van der et al. (1995) *Vaccine* 13: 401–407] or TbpB.

Antigens which are not desirable would include the group B capsule sialylated LPS antigens which have been shown to inhibit adherence to and invasion of epithelial and or endothelial cells by viable meningococci suggesting that interaction of the NOMV with the mucosal cell surface may be decreased by the presence of capsular polysaccharide and/or sialylated LPS on the NOMV.

Therefore, it may be advantageous to delete genes coding for the reduction modifiable protein (Rmp) which has been shown to induce antibodies that may block bactericidal activity of other antibodies under certain conditions. It appears to be desirable to block sialic acid synthesis and thereby prevent expression of capsule (in *N. meningitidis* groups B, C, Y and W135) and sialylated LPS. One may also want to block expression of LPS types that include the Lacto-N-neotetraose group which is crossreactive with precursors of blood group antigens.

A further desirable characteristic of the vaccine strain is the expression of Opc protein which is known to function as an adhesin and/or an invasin. It is likely that this protein is able to bind to specific receptors on the cells at the mucosal surface and thereby enhance the immunogenicity of the vaccine. This outer membrane protein is subject to phase variation in expression. Mutants with constitutive expression of this protein can be prepared for example, by replacing the rmp protein which has stable expression, but may be an undesirable vaccine component, with a copy of the opc gene [van der Ley, P et al. 1995, ibid.; van der Ley, P. et al. (1992) *Infect. Immun.* 60: 3156–3161; Aho et al. (1991) *Mol. Microbiol.* 5: 1429–1437; Olyhoek et al. (1991) *Microbial Pathogenesis* 11: 249–257; Sarkari et al. (1994) *Mol. Microbiol.* 13: 207–217; Klugman et al. (1989) *Infect. Immun.* 57: 2066–2071]

The usefulness of the Opc protein as antigen in a NOMV intranasal vaccine is greater than in a parenteral vaccine because its expression may be necessary for adherence and invasion at the mucosal surface even though it may be later turned off when the bacterium enters the blood stream and becomes subject to killing by serum antibody and complement. It is also clear that NOMV prepared from certain multivalent vaccine strains developed by other investigators could be used in the preparation of this type of vaccine. Multivalent strains such as strains 1–2B-, PL16215, PL10124, and PL9146 described by van der Ley et al. [1995, ibid.]or the PorA hybrid strains TR516 or TR7216 described by van der Ley [1993, ibid.] could be used to prepare NOMV vaccines with a broader range of protection. The multivalent PorA strains described in the first reference or similar strains are already being used to prepare vaccines based on deoxycholate extracted vesicles for parenteral use. The present invention would allow the more native NOMV vaccine to be made from these strains. If an analog of the htrB mutation described in *E. coli* [Karow et al. (1991) *J. Bacteriol.* 173:

743–750] and *Haemophilis influenzae* [Lee et al. (1995) *J. Biol. Chem.* 270: 27151–27159] were introduced into the vaccine strains the resultant mutants would be expected to be defective in lipid A biosynthesis and produce LPS (outer membrane) with much reduced endotoxin activity. The resulting NOMV would likely be safe for parenteral use and would likely be superior to the present vaccines made by deoxycholate extraction. A parenteral vaccine is one that is injected either intramuscularly, subcutaneously, or intradermally. A mucosal vaccine is one that is applied to appropriate mucosal surfaces such as the nose and throat, the lung, the gut (oral vaccine), the vagina, or the rectum. A vaccine that is safe as a mucosal vaccine may not be safe for parenteral use.

Accordingly, we have produced NOMV from a mutant vaccine strain that cannot synthesize sialic acid and therefore cannot make capsule nor sialylate its LPS. NOMV from this mutant strain were found to induce a higher bactericidal antibody response in rabbits vaccinated intranasally than NOMV from an isogenic wild type strain.

We have developed appropriate growth media and culture conditions that allow growth of the vaccine strain under conditions of limiting iron availability which results in expression of the iron uptake proteins including transferrin binding protein 2 and still results in a relatively good yield of bacteria. In addition, the LPS content of the NOMV from meningococci grown under these conditions is only about 20% relative to protein as compared to an expected 30% to 80% thus resulting in lower toxicity.

The preparation and use of this type of vaccine for other Gram negative infections is likely to be effective and have a number of advantages over current vaccine candidates. For example, NOMV prepared from a strain of *Neisseria gonorrhoeae* that lacks protein III and expresses the Opa protein has been shown to mediate adherence to epithelial cells [Virji, M. et al. (1993) *Mol. Microbiol.* 10: 499–510] and may be an effective vaccine against gonococcal disease when given intranasally or in the vagina or rectum [Plummer et al. (1994) *J. Clin. Invest.* 93: 1748–1755; Waldbeser et al. (1994) *Mol. Microbiol.* 13: 919–928; Kupsch et al. (1993) *EMBO J.* 12: 641–650]. *N. gonorrhoeae* NOMV from cells grown on solid or liquid medium can be produced using substantially the same procedures as for the meningococcus. Gonococcal vaccines that have been investigated thus far have been based on purified cell surface components such as pili and the outer membrane protein PorB. The LPS has also been shown to induce bactericidal antibodies. One study used parenteral priming with a synthetic peptide vaccine followed by boosting with a whole cell oral vaccine [Trees et al. (1994) *Proceedings of the Ninth International Pathogenic Neisseria Conference*, Winchester, England 26–30 Sept, p. 841]. The use of NOMV as a vaginal or rectal vaccine would probably require that the vaccine be combined with a gel or thick emulsion so that it would stay in place for a period of time when applied to the mucosa at those sites.

Extension of this vaccine concept to other Gram negative bacteria other than Neisseria would be a little more complex but within the skill of a person in the art. The main issue for other (non-Neisseria) Gram negative bacteria is that the outer membrane is much more tightly associated with the peptidoglycan layer than is the case for the Neisseria. It is therefore more difficult to prepare substantial quantities of outer membrane vesicles from these organisms. Several of the outer membrane proteins that are missing or different in Neisseria are important in the close association of the outer membrane and the cell wall peptidoglycan of other species. In *E. coli*, for example, one of these is the lipoprotein discovered by Braun [Braun, V. (1975) *Biochim. Biophys. Acta* 415:335–377] that is coded for by the lpp gene and is covalently linked to the peptidoglycan at the carboxy terminus. This protein, which appears to be missing in Neisseria, is substituted at the amino terminus with lipid that integrates in the phospholipid bilayer of the outer membrane. A second protein in *E. coli* is OmpA which consists of two main parts or domains. One part loops in and out of the outer membrane and the second part connected by a hinge region protrudes down into the periplasmic space and interacts with the peptidoglycan. A paper published in 1978 by Sonntag et al.[*J. Bacteriol.* 136:280–285] described a double mutant lacking both the lpp coded lipoprotein and OmpA. This mutant grew reasonably well on media containing increased levels of magnesium and exhibited a circular morphology with abundant blebbing of the outer membrane which appeared in electron micrographs to be very loosely associated with the rigid peptidoglycan layer. Thus, by introducing mutations into a prospective vaccine strain of *E. coli* or other Gram negative bacterium that knocks out the Braun lipoprotein and OmpA proteins (or equivalent OMPs in other species) one could easily obtain good yields of outer membrane vesicles using substantially the same methods used for Neisseria.

The LPS of a number of Gram negative pathogens has been identified as a dominant antigen capable of inducing protective antibodies, but it is typically a poor immunogen by itself. Thus efforts have been made to covalently conjugate the LPS to a carrier protein or non-covalently complex the LPS to proteosomes in order to enhance its immunogenicity. In these cases the use of NOMV prepared from the homologous pathogen may be a highly effective solution to the problem of increasing the LPS immunogenicity.

This invention also relates to a more efficient method for producing NOMV. A general method for preparing NOMV from *N. meningiditis* was developed and published a number of years ago [Zollinger, W. D et al. (1979) *J. Clin. Invest.* 63:836–848]. This method has been successfully used for many years, but is not highly conducive to scaled up production because of two required ultracentrifugation steps.

We have currently demonstrated that the ultracentrifugation steps can be eliminated by use of batch-wise adsorption of nucleic acid onto a DEAE ion exchange matrix followed by filtration to remove the ion exchange matrix and then utlrafiltration using a membrane having a MWCO >500,000 or microfiltration using a membrane with a pore size of 0.1 μm or less, for example, an AG Technology Corp., Needham MA, Ultrafiltration cartridge CFP-1-E-6A. The ultracentrifugation steps were used to separate the NOMV from the smaller or more soluble nucleic acid, capsular polysaccharide (if expresed), periplasmic and other soluble proteins. Attempts to collect the NOMV without first doing the DEAE treatment were unsuccessful, resulting with NOMV which were not free of nucleic acid. The use of the correct membrane size is important and is preferably between the largest ultrafiltration pore size of about 500,000 MWCO and the smallest microfiltration pore size of about 0.1 μm. The soluble proteins, residual nucleic acid, and soluble capsular polysaccharide pass through the membrane while the vesicles which are approximately 0.1 μm diameter are retained and can be concentrated. This improvement in processing decreases substantially the time and cost of preparing large quantities of NOMV.

In one embodiment, the present invention relates to a vaccine for protection against *N. meningitidis*. The vaccine comprises native outer membrane vesicles from *N. meningitidis*. The vaccine can be prepared by isolating native outer membrane vesicles from the organism or from the culture medium by methods known in the art or methods described in this application. The purified NOMVs are prepared for administration to mammals by methods known in the art, which can include filtering to sterilize the solution, diluting the solution, adding an adjuvant and stabilizing the solution. Adjuvants which enhance production of NOMV specific antibodies include, but are not limited to, various oil formulations such as stearyl tyrosine (ST, see U.S. Pat. No. 4,258,029), the dipeptide known as MDP, saponin, aluminum hydroxide, and lymphatic cytokine. Mucosal adjuvants include cholera toxin B subunit (CTB), a heat labile enterotoxin (LT) from *E. coli* (a genetically toxoided mutant LT has been developed), and Emulsomes (Pharmos, LTD., Rehovot, Israel). The adjuvant alum (aluminum hydroxide) or ST may be used for administration to humans.

The vaccine can be lyophilized to produce a vaccine against *N. meningiditis* in a dried form for ease in transportation and storage. Further, the vaccine may be prepared in the form of a mixed vaccine which contains the NOMVs described above and at least one other antigen as long as the added antigen does not interfere with the effectiveness of the vaccine and the side effects and adverse reactions are not increased additively or synergistically. The vaccine can be associated with chemical moieties which may improve the vaccine's solubility, absorption, biological half life, etc. The moieties may alternatively decrease the toxicity of the vaccine, eliminate or attenuate any undesirable side effect of the vaccine, etc. Moieties capable of mediating such effects are disclosed in *Remington's Pharmaceutical Sciences* (1980). Procedures for coupling such moeities to a molecule are well known in the art.

The vaccine may be stored in a sealed vial, ampule or the like. The present vaccine can generally be administered in the form of a spray for intranasal administration, or by nose drops, inhalants, swabs on tonsils, or a capsule, liquid, suspension or elixirs for oral administration. In the case where the vaccine is in a dried form, the vaccine is dissolved or suspended in sterilized distilled water before administration. Any inert carrier is preferably used, such as saline, phosphate buffered saline, or any such carrier in which the NOMV vaccine has suitable solubility.

Generally, the vaccine may be administered orally, subcutaneously, intradermally or intramuscularly but preferably intranasally or orally in a dose effective for the production of neutralizing antibody and resulting in protection from infection or disease. The vaccine may be in the form of single dose preparations or in multi-dose flasks which can be used for mass vaccination programs. Reference is made to *Remington's Pharmaceutical Sciences*, Mack Publishing Co., Easton, Pa., Osol (ed.) (1980); and *New Trends and Developments in Vaccines*, Voller et al. (eds.), University Park Press, Baltimore, Md. (1978), for methods of preparing and using vaccines.

In another embodiment, the present invention relates to a method of reducing *N. meningitidis* infection symptoms in a patient by administering to said patient an effective amount of NOMV antibodies including those made in humans, either polyclonal or combinations of monoclonals to NOMV, as described above. When providing a patient with NOMV antibodies, the dosage administered will vary depending upon such factors as the patient's age, weight, height, sex, general medical condition, previous medical history, etc. In general, it is desirable to provide the recipient with a dosage of the above compounds which is in the range of from about 1 pg/kg to 500 mg/kg (body weight of patient), although a lower or higher dosage may be administered.

Described below are examples of the present invention which are provided only for illustrative purposes, and not to limit the scope of the present invention. Other suitable modifications and adaptations of the variety of conditions and parameters normally encountered in this art which are obvious to those skilled in the art are within the spirit and scope of the present invention.

The following methods and materials were used in the examples below.

Bacterial Strains. The *N. meningiditis* strain 9162 (B:15: P1.3: P5.10, NT:L3,7) is a case isolate from the CSF of a patient in Iquique, Chile in 1990. Beginning with this strain a mutant was constructed by deleting a portion of the synX gene and inserting a kanamycin marker. SynX is a gene in the biosynthetic pathway of sialic acid, and the mutation resulted in the inability to make the group B capsule or to sialylate the LOS. This strain 9162 synX(−) was used as the vaccine strain for most of the examples given.

The synX(−) mutant was constructed based on results and sequence information reported by Swartley and Stephens [Swartley and Stephens (1994) *J. Bacteriol.* 176: 1530–1534] who showed that insertion of a transposon, Tn916, into the synx gene led to a capsule negative phenotype. The same or an equivalent mutation could quite easily be introduced into any transformable *N. meningiditis* strain by someone trained in the art. A plasmid for use in transforming meningococci was constructed using the following procedure. Three DNA sequences were pieced together using the splicing by overlap extension (SOE) polymerase chain reaction (PCR) technique [Horton et al. (1989) Gene 77: 61–65]. The three DNA sequences included, in order beginning at the 5' end, synXB bases 67 to 681; the kanamycin resistance gene from pUC4K (Pharmacia LKB Biotech Co.) 671 to 1623; and synxB bases 886 to 1589. In addition, at the 5' end, a putative uptake sequence, ACCGTCTGAA, was added by including it at the end of the PCR primer used to amplify the synXB 67 to 691 base sequence. The complete construct was amplified by PCR, purified and blunt ligated into pUC19. pUC19 was used to transform *Escherichia coli* DH5α and selected on LB agar with 50 μg kanamycin. A kanamycin resistant colony was selected, the DNA extracted, purified, and cut with XbaI. Another copy of the presumptive uptake sequence was ligated into this multiple cloning region site and the resulting plasmid again used to transform *E. coli* DH5α and kanamycin resistant colonies screened by PCR for presence of the additional uptake sequence. Plasmid DNA was isolated from a selected colony and used as a template for PCR using primers that amplified only the insert part of the plasmid excluding the ampicillin resistance gene which should not be introduced into *N. meningitidis*. The amplified DNA was then purified and used to transform *N. meningitidis* strain 9162. The synX(−) mutant of *N. meningitides* was selected by kanamycin resistance and confirmed by PCR amplification of the modified region.

The Lpp(−) OmpA(−) double mutant of *E. coli* was obtained from Dr. Ulf Henning, Tuebingen, Germany and is described in a paper by Sonntag, et al. [Sonntag, I et al. (1978) *J. Bact.* 136:280–285].

Growth media. Meningococci were plated from frozen stocks on GC agar medium (Difco Laboratories, Detroit, Mich.) with 1% v/v defined supplement [Schneider, H. et al. (1988) *Infect. Immun.* 56:942–946].

The growth of *Neisseria meningitidis* in liquid medium with limiting iron to induce expression of the iron uptake proteins was done using medium with the following composition and without the specific addition of an iron chelator such as desferol. The medium is modified from that published by BW Catlin [Catlin BW. (1973) *J. Infect. Dis.* 128:178–194] by replacing several individual amino acids with 1% casamino acids (certified, Difco Laboratories). The medium contained per liter, 0.4 g $NH_4Cl$, 0.168 g KCl, 5.85 g NaCl, 1.065 g $Na_2HPO_4$, 0.17 g $KH_2PO_4$, 0.647 g sodium citrate, 6.25 g sodium lactate (60% syrup), 0.037 g $CaCl_2.2H_2O$, 0.0013 g $MnSO_4.H_2O$, 5 g glycerol, 0.02 g cysteine, 10 g casamino acids, 0.616 g $MgSO_4$, and distilled water to one liter. The same iron deficient medium was used for the starter flasks and the final culture flasks or fermenters.

*Escherichia coli* cultures were grown on Luria broth or Luria agar (Difco Laboratories).

Buffers. TES buffer for extraction of NOMV from pelleted cells contained 0.05 M Tris-HCl, 0.01 M EDTA, 0.15 M NaCl, pH 7.5.

Serological Assays. Bactericidal assays were performed as described by Moran et al. [Moran, et al. (1994) *Infect. Immun.* 62:5290–5295] using the parent encapsulated strain 9162 as the test strain. ELISA assays were performed according to the quantitative method described by Zollinger et al. [(1986) In: N. R. Rose and H. Friedman [Eds.] *Manual of Clinical Immunology*, Third Edition, American Society For Microbiology, Washington, D.C, p. 346]. Where reagents were available to set up a standard curve, the results were calculated as $\mu g$ antibody per ml. In other instances the results are reported as ELISA units which was calculated as the product of the optical density and the reciprocal dilution. In both instances the result was calculated for two or three points in the linear range of the curve (approximate OD range 1.0 to 0.15) and the average reported.

Polyacrylamide gel electrophoresis. The NOMV preparations were analyzed by sodium dodecyl sulfate polyacrylamide gel electrophoresis by the method of Laemmli [Laemmli, U.K. (1970) *Nature* (London); 227:680–685].

EXAMPLE 1

Small Scale Production of NOMV from Strains 9162 and 9162 synX (−).

A. Growth of *N. meningiditis* Strains 9162 and 9162 synX(−)

The bacterial strains were stored as frozen cultures in skim milk. The same method was used to prepare NOMV from the parent strain 9162 and the mutant sialic acid deficient strain 9162 synx(−). The strain to be grown was streaked for isolation on agar GCDS plates and incubated overnight (14–16 hrs) at 37° C. in a candle extinction box. The following day, the growth from about half a plate comprising mostly isolated colonies was used to inoculate 100 ml of sterile modified Catlin's medium without iron in a 500 ml Erlenmeyer flask. The flask was placed on a rotary shaker at 370° C. and 180 rpm and allowed to grow for 4 to 6 hours. At the end of that time the purity and optical density at 600 nm of the cultures was verified and the contents of the flask used to inoculate one liter of sterile modified Catlin's medium without iron in a 2800 ml Fernbach flask. The culture was grown on a rotary shaker at 37° C. and 120 to 180 rpm for 8 hours. The culture was checked for purity by Gram stain, inactivated by addition of phenol to 0.5% and incubated at room temperature for 2 hours.

The cells were harvested by centrifugation at 5000×g for 30 min using 1 liter bottles in a JS 5.2 rotor (Beckman Instruments, Inc., Palo Alto, Calif.). The pelleted cells were combined and weighed. The yield was 8 gm packed cells per liter of culture. The packed cells were kept frozen until further processing.

B. Preparation of NOMV from Cell Paste

NOMV was extracted from the cells by a modification of a well known method [Zollinger, et al. (1979) *J. Clin. Invest.* 63:836–848]. Briefly, the cells were suspended in 5 volumes of TES buffer pH 7.5 and warmed at 54–56° C. for 30 min. The cell suspension was then cooled to room temperature and sheared in a Omnimixer (Dupont Instruments-Sorvall, DuPont Co., Newtown Conn.) at top speed for 3 minutes. The resulting suspension was centrifuged at 23,500×g for 20 minutes and the supernatant collected and set aside. The pellets were re-extracted with distilled water using one-half the volume of the supernatant from the first extraction. The cells were not reheated but were sheared in the Omnimixer at top speed for 3 minutes. The cell suspension was centrifuged at 23,500×g for 20 min and the supernatants combined. The cell pellets were discarded. The combined supernatants were centrifuged again at 23,500×g for 15 min and the pellets discarded.

The extract supernatant was ultracentrifuged at 186,000×g for 60 min at 4° C. The supernatant was discarded and the resulting pellets were thoroughly suspended in distilled water at one-half the original supernatant volume. The solution was then centrifuged at 10,000×g for 10 minutes to remove any large aggregated material and the supernatant re-centrifuged at 186,000×g for 60 min. The supernatant was discarded and the pellets thoroughly resuspended in one-tenth the original extract supernatant volume of distilled water. The purified NOMV was filter sterilized and assayed for protein.

EXAMPLE 2

Intranasal Vaccination of Rabbits With NOMV from Parent (9162) and Sialic Acid Deficient Mutant (9162 synX(−)) Strains of Meningococci The humoral and mucosal response of rabbits to intranasal vaccination with NOMV was investigated using NOMV prepared from strain 9162 (Lot D190894) and from the sialic acid deficient mutant of this strain 9162 synx(−) (Lot E110195). The second objective was to determine if the presence or absence of capsule and sialylated LOS affected the immunogenicity of the NOMV.

Unanesthetized rabbits were intranasally immunized at days 0, 28, and 56. Each of the two NOMV vaccines was administered to four rabbits at 100 $\mu g$ protein per dose. An additional group of rabbits received normal saline in place of vaccine. Rabbits were weighed to the nearest gram at days 0, 4, and 7 to grossly examine for any acute toxic effects of the vaccines. Bleeds and nasal washes were taken at days 0, 14, 28, 42, 56, and 70. Lung lavages and mouth swabs (to examine salivary antibody) were done after euthanasia at day 70. Serum bactericidal activity was assayed using the parent capsule positive strain as the test strain, and meningococcal-specific serum IgG and IgA was measured using an ELISA with lot E110195 NOMV or purified LOS as antigen. The amount of meningococcal-specific IgA was also measured by ELISA in nasal wash, saliva, and lung lavage samples using lot E110195 NOMV as antigen.

Figure 1:
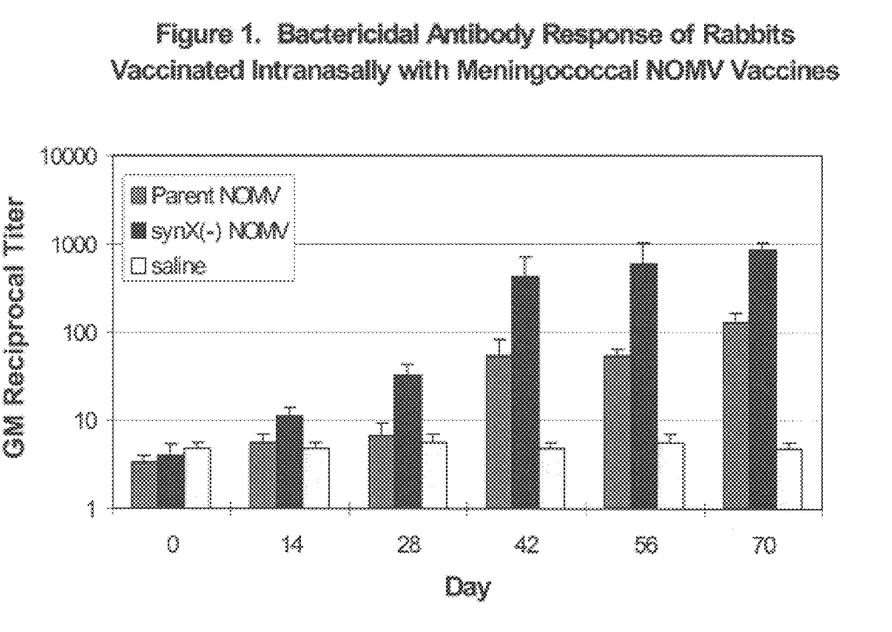
Figure 2:
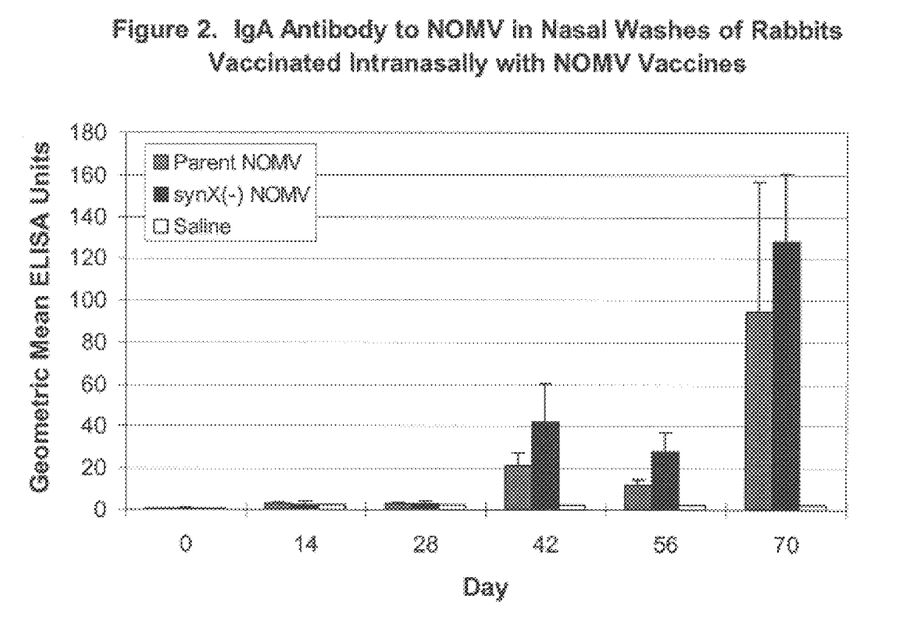
FIG. 2. IgA antibody to NOMV measured by enzyme linked immunosorbant assay (ELISA) in the nasal washes of rabbits vaccinated intranasally with NOMV vaccines. Rabbits were vaccinated as indicated in the description of FIG. 1. NOMV from the synX(−) mutant strain was used as the antigen. Values are geometric mean reciprocal values expressed as ELISA units (the mean of the product of the dilution and the optical density at 405 nm taken at 2 or 3 points in the optical density range of 0.1 to 1.0). The error bars represent 1 standard error of the geometric mean.
Figure 3:
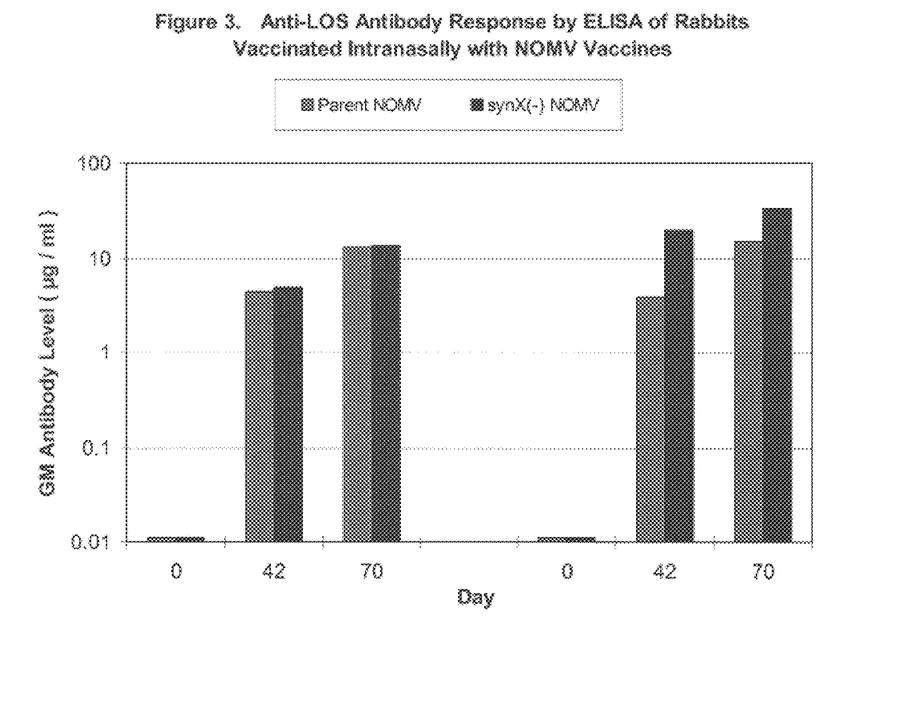
FIG. 3. Antibody to meningococcal lipooligosaccharide (LOS) in sera of rabbits vaccinated intranasally with NOMV vaccines. Rabbits were vaccinated as indicated in the description of FIG. 1. Purified LOS of immunotypes L3,7 and L8 were used as antigen in the assay. Results are expressed as geometric mean micrograms per milliliter of specific antibody. The error bars represent 1 standard error of the geometric mean.

The mean weight for each group of rabbits increased at day 4 and 7 and no adverse side effects were noted in any rabbits based upon gross observation. The serum bactericidal antibodies of rabbits immunized intranasally with the NOMV vaccines increases 30 to 200 fold after three doses. The bactericidal antibody titers of rabbits vaccinated with lot E110195 NOMV from the synX(−) strain rose sooner and to higher levels than rabbits immunized with parent NOMV (FIG. 1). NOMV from both meningococcal strains induced a local mucosal antibody response, as seen by the sharply increased levels of anti-NOMV IgA antibodies in nasal washes (FIG. 2). Specific serum IgG and IgA antibodies increased strongly after vaccination with either NOMV vaccine (table 1). In addition, increased levels of NOMV specific IgA antibodies were observed in saliva and lung lavage fluids. NOMV from the mutant strain, however, induced the highest amount of lung lavage IgA (table 1). Immunoblotting using serum from 2 rabbits each in groups 1 and 2 indicated that meningococcal-specific IgG antibodies were directed at a wide variety of immunoreactive bands, including class 1, 3, 4, and 5 proteins, LOS, and several high molecular weight proteins that may include the transferrin-binding proteins (data not shown). The antibody response to the L3,7 and L8 immunotypes of LOS was quantitatively determined by ELISA. Although the NOMV vaccine contained predominantly L3,7 LOS, 100 to 1000 fold increases in antibodies to both the L3,7 and L8 LOS were induced (FIG. 3).

Conclusions: The NOMV vaccines given intranasally did not cause any detectable weight loss or other acute toxic effects. NOMV from the noncapsular mutant (synx(-) NOMV) induced a higher bactericidal response than NOMV from the encapsulated parent NOMV. Intranasal immunizations with NOMV induced high levels of meningococcal-specific serum IgG and IgA antibodies by ELISA. Intranasal immunization with NOMV vaccines induced a local meningococcal-specific mucosal response as shown by the high levels of IgA in nasal wash, saliva, and lung lavage samples. The serum antibody response was directed against a variety of surface antigens, including the class 1, 3, 4, and 5 proteins, LOS, and several high molecular weight proteins.

TABLE 1

Antibody responses of rabbits to intranasal vaccination with NOMV vaccines by ELISA with synX (-) NOMV used as antigen

| Fluid | Antibody isotype | Saline | Antibody level at day 70 after vaccination with indicated vaccine | |
|---|---|---|---|---|
| | | | Parent NOMV | synX (-) NOMV |
| Serum | IgG (µg/ml) | 7.01 | 1560 | 1767 |
| Serum | IgA (ELISA units) | 6.9 | 1514 | 1242 |
| Lung washes | IgA (ELISA units) | 0.76 | 71.9 | 222 |
| Saliva/ mouth swab | IgA ELISA units) | 0.39 | 18 | 17.7 |

EXAMPLE 3

GMP Production of NOMV. Lot #0123 and Testina for Safety and Potency

A production lot of NOMV vaccine was produced from strain 9162 synX(-) under good manufacturing conditions for testing in human volunteers. The vaccine was tested in preclinical safety and immunogenicity studies.

Production of Cell Paste. A master seed lot and a production seed lot of *N. meningiditis* strain 9162 synX(-) were prepared and stored frozen at -70° C. in Greave's solution. A vial of the production seed was thawed and used to inoculate 6 agar plates containing GC medium with defined supplement. The plates were grown overnight at 37° C. in a 5% $CO_2$ atmosphere and the following day the growth from each two plates was suspended in 10 ml of sterile, modified Catlin's medium without iron and used to inoculate 1 liter of modified Catlin's medium without iron in a 2800 ml Fernbach flask. The three inoculated Fernbach flasks were incubated on a rotary shaker at 37° C. operating at 180 cycles per min for 5.5 hours. At the end of this time the optical density of the cultures was determined and the purity of the cultures verfied by Gram stain. The three liters of culture were then used to inoculate 27 liters of modified Catlin's medium without iron in a 40 liter fermenter. The culture was grown for 3 hours in the 40 liter fermenter and then used to inoculate 270 liters of modified Catlin's medium without iron in a 300 liter fermenter. The culture was grown in the 300 liter fermenter for 4 hours at which time the culture had reached stationary phase. The culture was then inactivated by addition of phenol to a final concentration of 0.5%. After 2 hours the culture was harvested by centrifugation in a continuous flow Sharples AS26SP centrifuge (Alfa-Laval Separation, Inc., Warminster, Pa.). The yield was 839 grams of cell paste which was stored frozen. This was about 30–35% of the yield of a comparable fermentation with excess iron in the medium.

Figure 4:
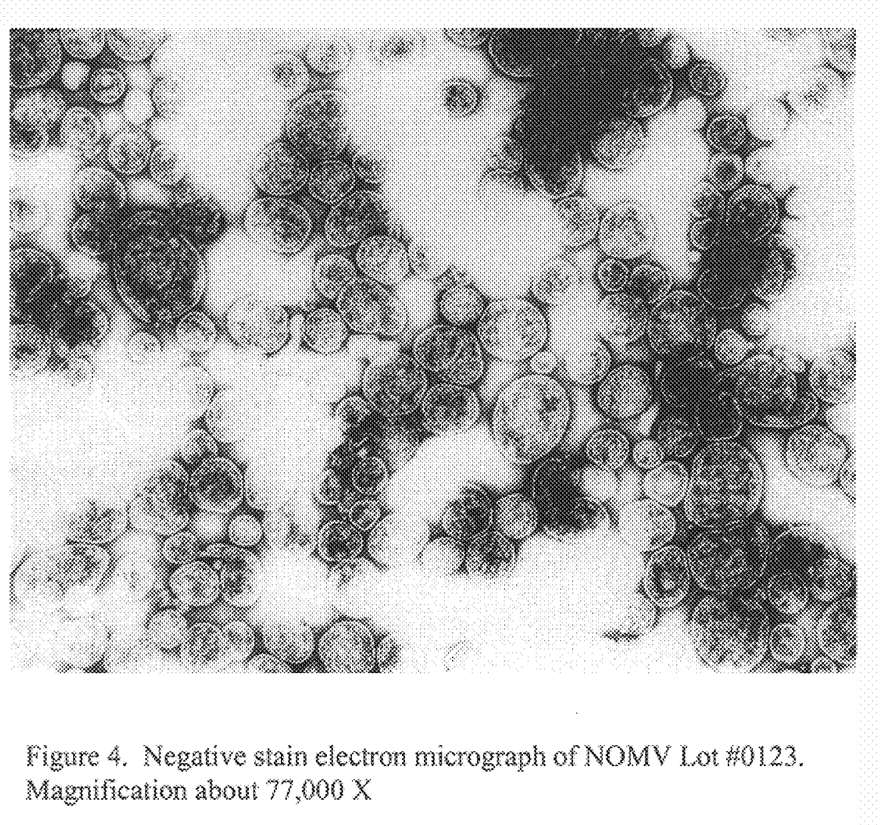
FIG. 4. Electron micrograph of NOMV lot #0123 taken after negative staining with phosphotungstic acid. Magnification about 77,000×.
Figure 5:
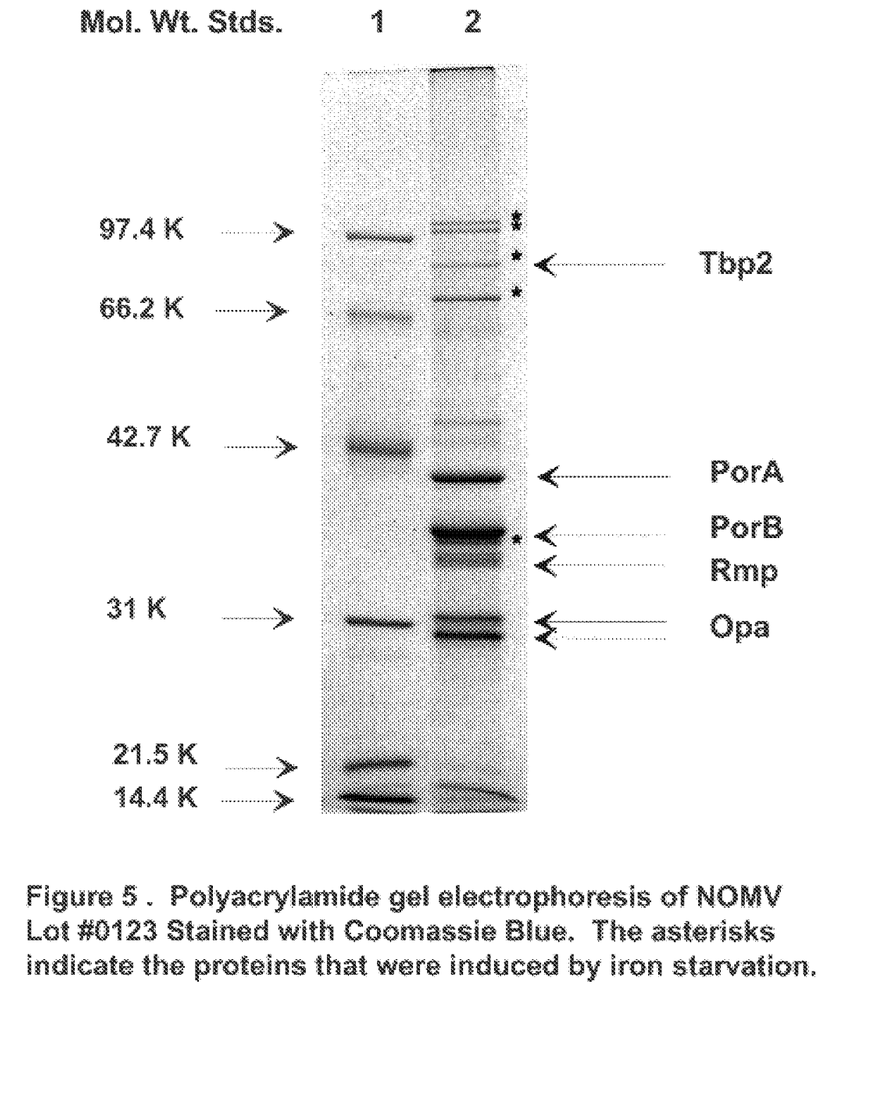
FIG. 5. Polyacrylamide gel electrophoresis of NOMV lot #0123 and protein molecular weight standards. The asterisks indicate the proteins that were induced by iron starvation. The arrows at the right identify principal outer membrane protein antigens: Tbp2=transferrin binding protein 2, PorA= porin A also called the class 1 protein or subtype protein, PorB=porin B also called the class 3 or serotype protein, Rmp=reduction modifiable protein or class 4 protein, Opa= opacity proteins (2 are indicated) or class 5 protein.
Figure 6:
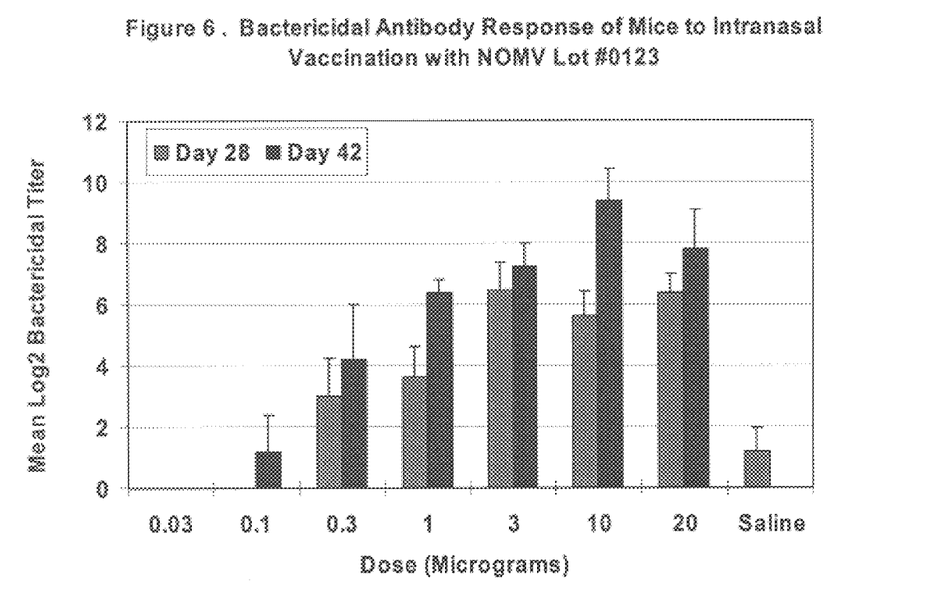
FIG. 6. Bactericidal antibody response of mice to intranasal vaccination with 9162 synX(−) NOMV lot #0123. Groups of 5 mice were vaccinated intranasally on days 0 and 28 with 25 µl of vaccine containing the indicated amount of NOMV. A separate group was vaccinated with normal saline as a control. Pre-vaccination levels measured on a separate group were <1:2. The mice were bled on days 28 and 42. The mouse sera were tested against the encapsulated parent strain 9162 using normal human serum as a source of complement.
Figure 7:
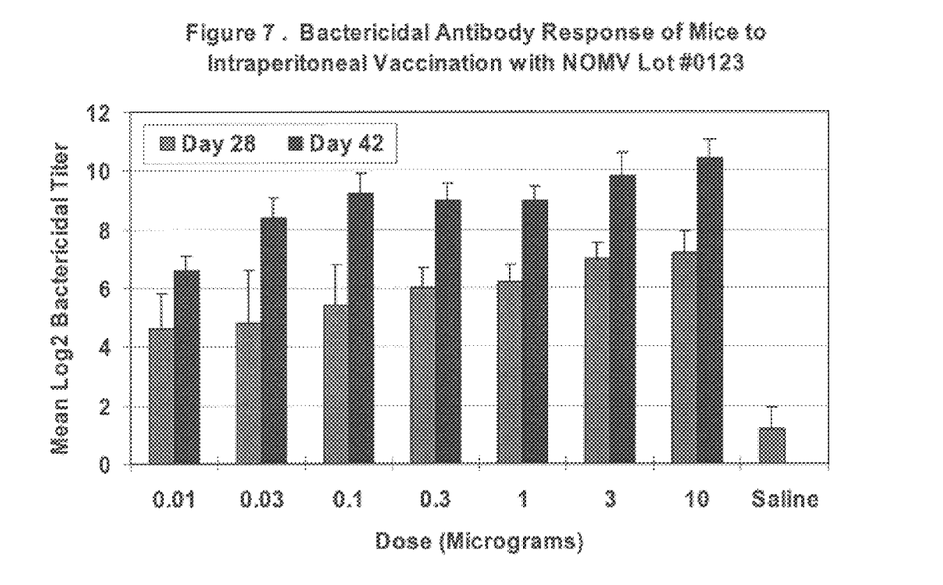
FIG. 7. Bactericidal antibody response of mice to intraperitoneal vaccination with 9162 synX(−) NOMV lot #0123. Groups of 5 mice were vaccinated intraperitoneally on days 0 and 28 with 100 µl of vaccine containing the indicated amount of NOMV. A separate group was vaccinated with normal saline as a control. Pre-vaccination levels measured on a separate group were <1:2. The mice were bled on days 28 and 42. The mouse sera were tested against the encapsulated parent strain 9162 using normal human serum as a source of complement.
Figure 8:
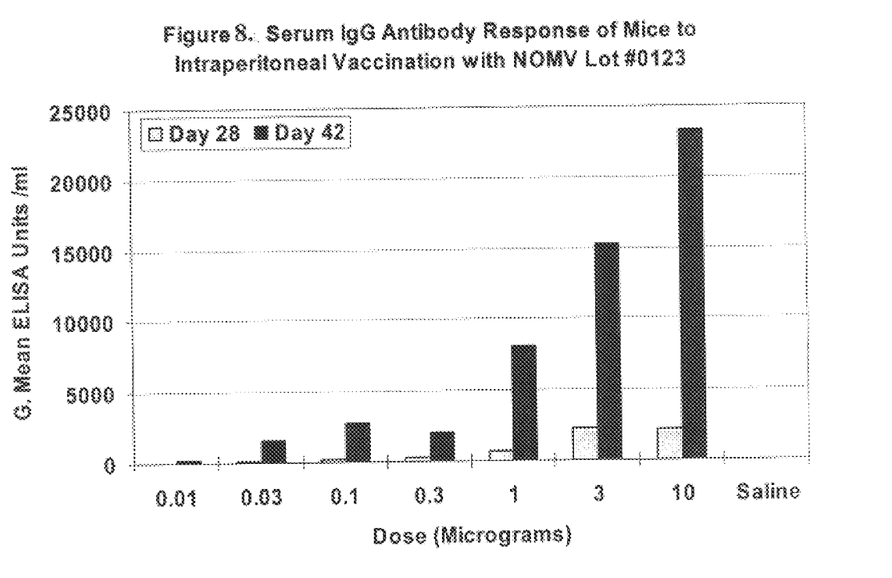
FIG. 8. Serum IgG antibody response of mice to intranasal vaccination with NOMV Lot #0123 by ELISA. NOMV from the parent 9162 strain was used as the antigen. Mice were vaccinated as indicated in description of FIG. 6. Data are expressed as the geometric mean ELISA units (see description for FIG. 2) of specific IgG antibody per milliliter of serum. The bars indicate one standard error of the mean.
Figure 9:
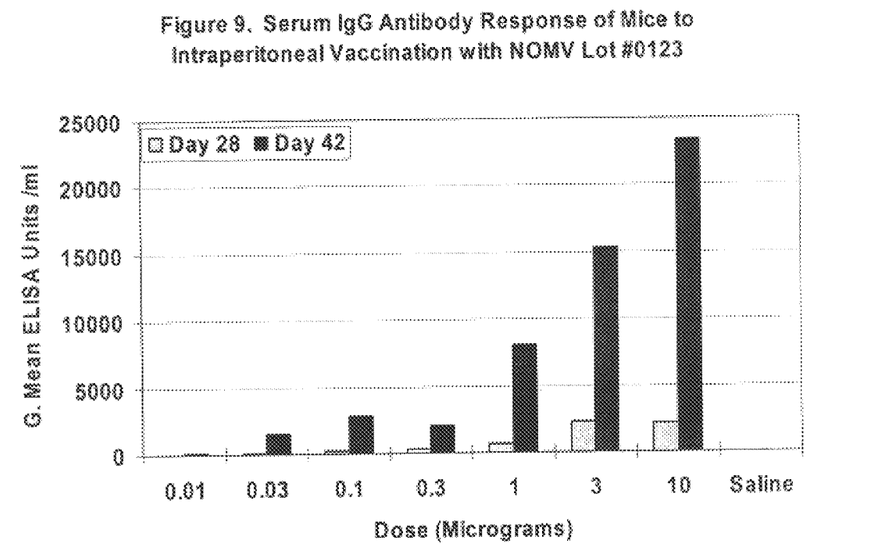
FIG. 9. Serum IgG antibody response by ELISA of mice to intraperitoneal vaccination with NOMV Lot #0123. NOMV from the parent 9162 strain was used as the antigen. Mice were vaccinated as indicated in description of FIG. 6. Data are expressed as the geometric mean ELISA units (see description for FIG. 2) of specific IgG antibody per milliliter of serum. The bars indicate one standard error of the mean.
Figure 10:
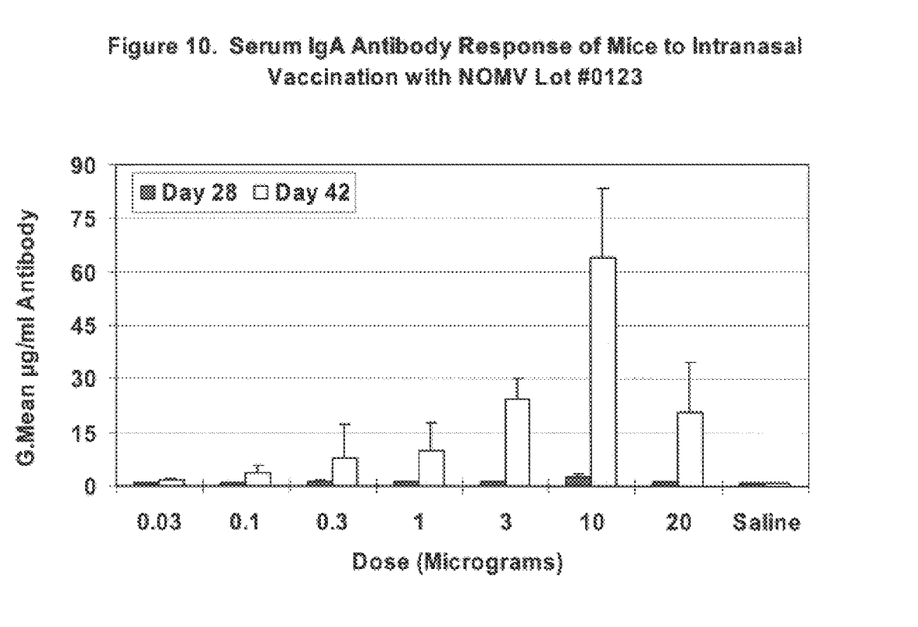
FIG. 10. Serum IgA antibody response of mice to intranasal vaccination with NOMV Lot #0123 by ELISA. NOMV from the parent 9162 strain was used as the antigen. Mice were vaccinated as indicated in description of FIG. 6. Data are expressed as the geometric mean micrograms of specific IgA antibody per milliliter of serum. The bars indicate one standard error of the mean.
Figure 11:
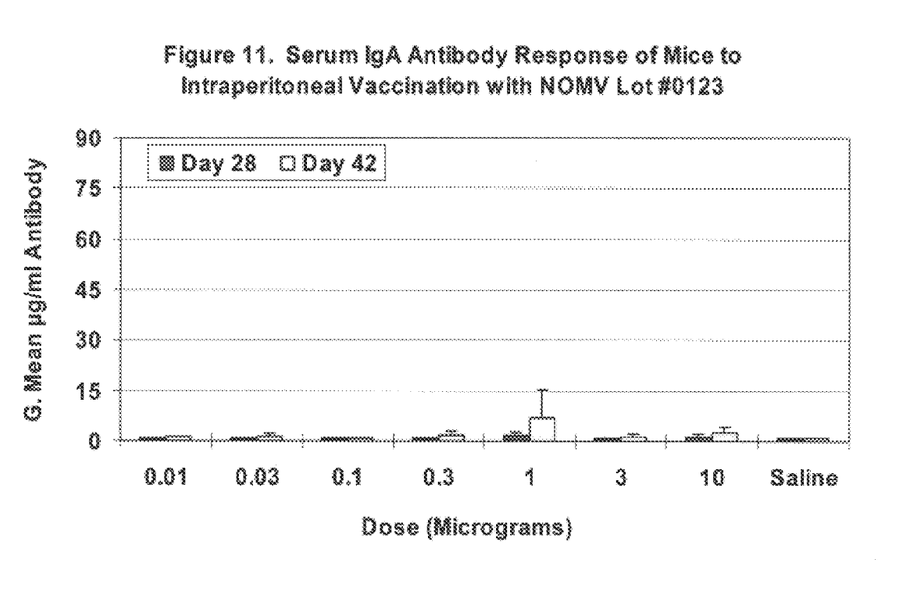
FIG. 11. Serum IgA antibody response by ELISA of mice to intraperitoneal vaccination with NOMV Lot #0123. NOMV from the parent 9162 strain was used as the antigen. Mice were vaccinated as indicated in description of FIG. 6. Data are expressed as the geometric mean micrograms of specific IgA antibody per milliliter of serum. The bars indicate one standard error of the mean.
Figure 12:
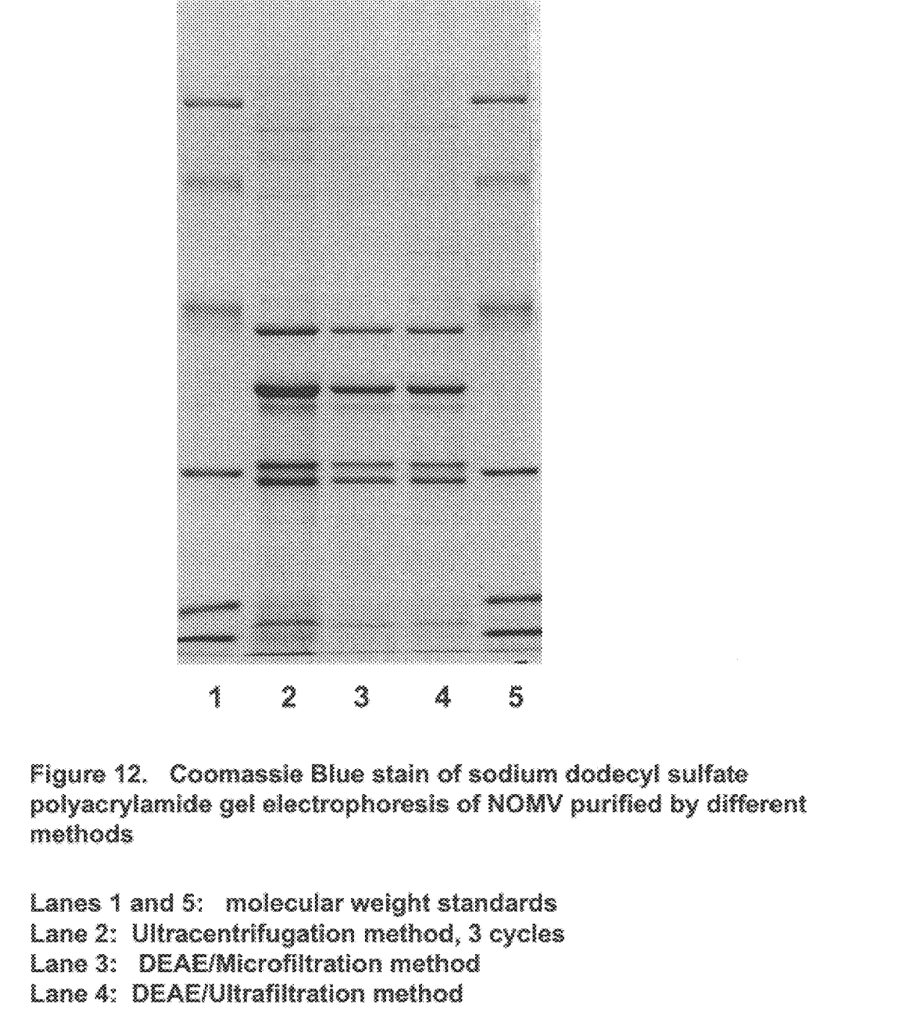
FIG. 12. Polyacrylamide gel electrophoresis of NOMV purified by different methods. The gel was stained with Coomassie Blue. Lanes 1 and 5 are molecular weight standards with molecular weights as shown in FIG. 5; lane 2, NOMV purified by 3 cycles of ultracentrifugation; lane 3, NOMV purified by new DEAE/Microfiltration method; lane 4, NOMV purified by new DEAE/ultrafiltration method.

Preparation of NOMV from Cell Paste. The cell paste (414 gm) was thawed and suspended in 6 volumes of TES buffer at room temperature. The suspension was divided into two 4 liter flasks, placed in a 58° C. water bath and mixed periodically. After the temperature of the solution had reached 52 to 54° C. incubation was continued for 30 min. The suspension was removed from the water bath, cooled and sheared in 800 ml batches in a 1 liter Waring blender at high speed for 3 min. The suspension was then centrifuged at 23,500×g for 20 min using a GSA rotor in a Sorvall refrigerated centrifuge (Dupont Instruments/Sorvall, Newtown, Conn.). The supernatant was retained and the pellets were resuspended in 2.5 ml of distilled water per gram of cell paste processed. The suspension was sheared in the Waring blender as before and the suspension centrifuged as above at 23,500×g for 20 min. The pellets were discarded and the supernatants from the two extractions combined. The combined supernatant was recentrifuged at 23,500×g for 15 min at 4° C. and the pellets discarded. The final combined supernatant was then ultracentrifuged at 180,000×g for 60 min to pellet the NOMV. The pellets were resuspended in sterile saline equal to one-half the volume of the initial combined supernatant before ultracentrifugation. After thoroughly resuspending the pellets the solution was centrifuged at 16,000×g for 15 min, the pellets discarded, and the supernatant ultracentrifuged at 180,000×g for 60 min. The pelleted NOMV was suspended in a total of 250 ml of sterile saline. Analysis of the NOMV revealed that residual nucleic acid was above 1–2%. Accordingly, the NOMV was diluted to a total of 800 ml with water for injection and the NOMV pelleted a third time in the ultracentrifuge at 180,000×g for 60 min. The pelleted NOMV was suspended in 450 ml of sterile saline, sterile filtered through a 0.2 µm pore size membrane filter and stored at 4° C. The final vialed product was designated Lot #0123 and consisted of 10 ml vials containing 5 ml of NOMV in normal saline at 800 µg/ml protein, 220 µg/ml LOS. The final product was analyzed by polyacrylamide gel electrophoresis and by negative stain electron microscopy. The results of these analyses are shown in FIGS. 4 and 5.

Safety and Toxicity Testing. The final product NOMV lot #0123 was tested for pyrogenicity in rabbits by both the standard intravenous test (Code of Federal Regulations, Title 21, Section 610.13b) and also in a modification of the standard assay where the vaccine was given by the intranasal route (table 2). The NOMV was found to be several thousand fold less toxic when administered intranasally to rabbits than when administered intravenously. In the general safety/toxicity test (Code of Federal Regulations, Title 21, Section 610.11) the NOMV was found to be nontoxic at 50 $\mu$g in the mouse and 500 $\mu$g in the guinea pig. In the latter test the concentrations tested were based on dosage levels for parenteral vaccines rather than proposed intranasal dosages.

Table 2. Results of safety testing of Lot #0123 of NOMV vaccine.

TABLE 2

Results of safety testing of Lot #0123 of NOMV vaccine.

| Test | Dose of NOMV | Result |
|---|---|---|
| Standard Rabbit Pyrogen Test (Intravenous) | 0.1: μg per rabbit | Failed |
| Standard Rabbit Pyrogen Test (Intravenous) | 0.05: μg per rabbit | Passed |
| Intranasal Rabbit Pyrogen Test | 100: μg per rabbit | Passed |
| Intranasal Rabbit Pyrogen Test (24 hours) | 100: μg per rabbit | Passed |
| Non-GLP Intranasal Rabbit Pyrogen | 400: μg per rabbit | Passed |
| General Safety/Toxicity in Mice | 50 μg | Passed |
| General Safety/Toxicity in Guinea Pigs | 500 μg | Passed |

Potency Testing of NOMV Lot #0123 in Mice. Fifteen groups of 5 outbred CD1 white mice were vaccinated with NOMV vaccine Lot #0123. Groups 1 to 7 were vaccinated intranasally with 25 μl of vaccine containing dosages of 0.03, 0.10, 0.30, 1.0, 3.0, 10, or 20 μg of vaccine (protein). Five mice were given each dosage. Groups 9 to 15 were vaccinated intraperitoneally with 0.1 ml of vaccine containing 0.01, 0.03, 0.1, 0.3, 1.0, 3.0, or 10 μg of vaccine (protein). Group 8 received normal saline in place of vaccine. The indicated dosages were given at 0 and 28 days, and blood was drawn on days 28 and 42. The levels of antibodies in the sera were determined and compared to the group that received saline in place of vaccine. The sera were assayed by bactericidal assay which is a functional assay that has been correlated with protection and also by ELISA for total IgG and IgA antibodies to homologous NOMV. Both routes of immunization induced high titers of bactericidal antibodies to the encapsulated parent strain 9162, but intranasal vaccination required about 10-fold more antigen to achieve a comparable antibody response (FIGS. 6 and 7). ELISA assays also revealed that intranasal vaccination induced high levels of specific IgG antibodies (FIGS. 8 and 9) and IgA antibodies (FIGS. 10 and 11). Higher levels of IgA antibodies were induced with intranasal vaccination as compared to intraperitoneal vaccination, but lower levels of IgG antibodies were induced.

EXAMPLE 4

Improved Method for Large Scale Preparation of NOMV

Shake flask cultures of *N. meningiditis* strain 9162 synX (–) were grown and harvested as described in example 1. The procedure as described in example 1 was followed up to the first ultracentrifugation step. At this point in the process the crude extract was split in two parts. One part of the extract was processed as described below using steps that were substituted for the two ultracentrifugation steps (180,000×g for 60 min at 4° C.) used in examples 1 and 2 as a means of purifying the NOMV from the cell extract. The other part of the extract was processed by ultracentrifugation as described in example 1.

An amount of Whatman DE52 DEAE cellulose equal to two grams per 10 ml of cell extract was washed twice in about 10 volumes of TES extraction buffer and collected on a filter paper using a Buchner funnel fitted in a vacuum side arm flask. The cake of washed DEAE cellulose was then added to the cell extract and mixed at room temperature for 1 hour. After this time the DEAE cellulose was removed by passing the suspension through a Buchner funnel fitted with a suitable filter paper. The filtered solution was recovered and kept for further processing. After this step the extract was found to be essentially free of nucleic acid. Other DEAE ion exchange matricies may also be used in this procedure.

The extract was then processed by ultrafiltration using a 500,000 MWCO membrane or by microfiltration using a 0.1 μm pore size membrane (A/G Technologies Corp. Needham, Mass.) cartridges UFP-500-C4A and CFP-1-D-4A respectively. The ultrafiltration (or microfiltration) column was set up, cleaned, and used according to the manufacturer's instructions. The extract was added to the ultrafiltration system and cycled through the column using about 2 to 15 PSI back pressure and keeping the volume constant by continuous addition of 0.9% sodium chloride solution. The process was continued until 20 volumes of sodium chloride solution had passed through the membrane. The retentate was then concentrated to one tenth the original volume. The process was stopped and the retentate recovered from the column. Table 3 and FIG. 12 show the comparative results obtained with the DEAE/ultrafiltration method as compared to the normal ultracentrifugation method. The ultrafiltration cartridge and the microfiltration column gave similar results, although the flow rate was better with the ultrafiltration column. The data in table 3 and FIG. 12 show that the yield, composition and purity were very similar indicating that the new method could be used as an adequate substitution for the normal ultracentrifugation method.

TABLE 3

Comparative results of two methods for purifying the NOMV from crude cell extract.

| | | Ultracentrifugation | | DEAE/-Ultrafiltration | |
|---|---|---|---|---|---|
| Measurement | Crude extract | 2 cycles | 3 cycles | 500,000 MWCO | 0.1 μm pore size |
| Protein concentration | 380 | 44.3 | 40.2 | 46.6 | 47.0 |

TABLE 3-continued

Comparative results of two methods for purifying the NOMV from crude cell extract.

| Measure-ment | Crude extract | Ultracentrifugation | | DEAE/-Ultrafiltration | |
|---|---|---|---|---|---|
| | | 2 cycles | 3 cycles | 500,000 MWCO | 0.1 µm pore size |
| Nucleic acid concentration | 144 | 1.66 | 0.68 | 0.8 | 0.8 |
| $OD_{280nm}/OD_{260nm}$ | 0.54 | 0.96 | 1.23 | 1.21 | 1.21 |

EXAMPLE 5

Preparation of NOMV from *E. coli lpp(−), ompA (−)* Double Mutant

The feasibility of extending the NOMV vaccine approach to other gram negative organisms that, unlike Neisseria spp., do not have a loose outer membrane that naturally blebs off during growth was demonstrated by applying the method of preparing NOMV from the meningococcus to a double mutant of *E. coli* that is lacks both the Braun lipoprotein (Lpp) and OmpA.

The strain was streaked for isolation and grown at 37° C. overnight on Luria agar plates containing 30 mM $MgCl_2$. The growth from the plate was transferred to a one liter flask containing 200 ml of liquid Luria broth containing 30 mM $MgCl_2$ and grown overnight on a rotary shaker at 37° C. The purity and spherical morphology of the cells were verified by Gram stain. The cells were harvested by centrifugation at 16,000×g for 15 min, and NOMV harvested essentially as described for *N. meningitidis* in example 1 but modified for smaller scale. The cells (1.5 grams) were suspended in 20 ml of TES buffer at pH 7.5 and heated at 60° C. for 30 min. The suspension was then sheared in the Omnimixer at 90% of maximum speed for 1 min and the cells spun out by centrifugation at 16,000×g for 15 min. The supernatant was recovered and set aside, and the pellets were resuspended in 10 ml of TES buffer and reextracted by the same procedure. The two supernatants were combined. The NOMV were isolated from the crude extract by ultracentrifugation at 186,000×g for 75 min. The supernatant was discarded and the pellet suspended in 10 ml of distilled water and centrifuged at 16,000×g for 15 min. The low speed pellet was discarded and the supernatant was then ultra centrifuged at 186,000×g for 75 min. The resulting NOMV pellet was recovered and suspended in 2 ml of distilled water and filtered through a 0.45 µm pore size membrane filter.

Figure 13:
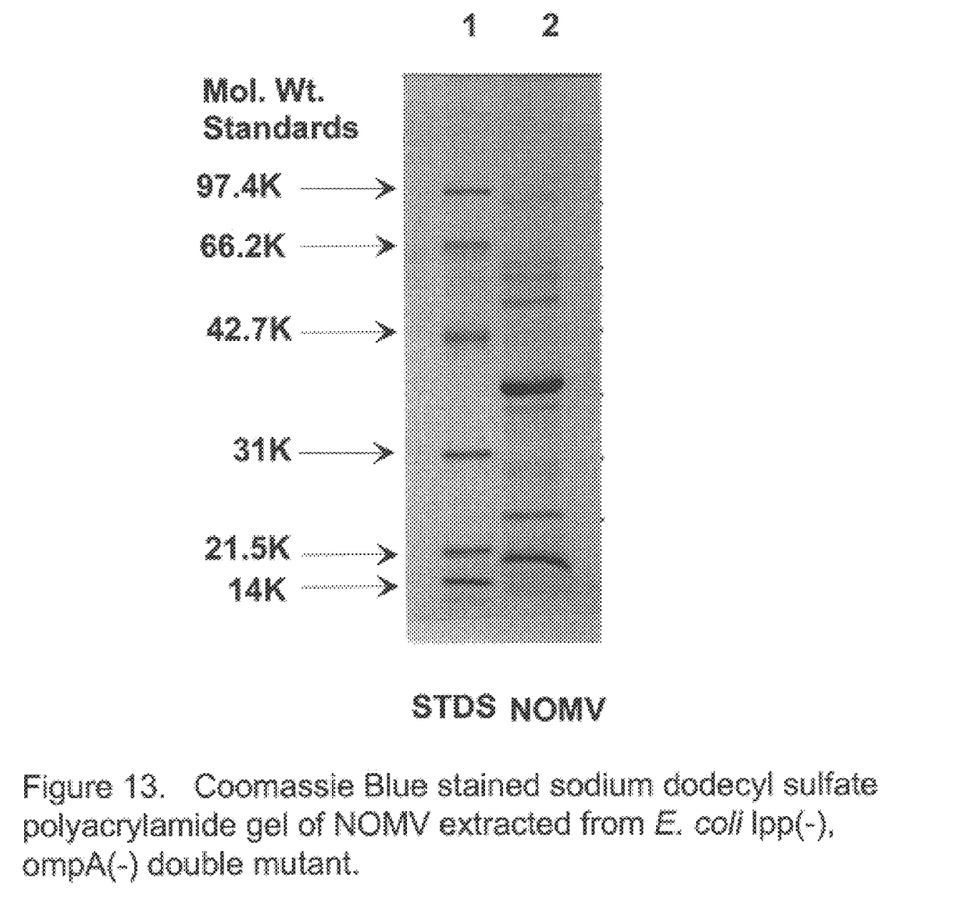
FIG. 13. Polyacrylamide gel electrophoresis of NOMV purified from *E. coli* lpp(-),ompA(-) with double mutation in outer membrane proteins and a loose outer membrane phenotype. The gel was stained with Coomassie Blue. Lane 1 is molecular weight standards and lane 2 is *E. coli* NOMV.

The NOMV was assayed for protein and the yield was calculated to be 3 mg of NOMV protein per 200 ml culture or 2 mg NOMV protein per gram of packed cells. This is approximately the same yield that is obtained from *N. meningitidis* cells. The *E. coli* NOMV was analyzed by polyacrylamide gel electrophoresis, and the results are given in FIG. 13. The protein band pattern is quite simple as expected for an outer membrane preparation with two deleted proteins. One major band is seen, probably a porin, and a number of minor bands. Further analysis of the *E. coli* NOMV is required, but these results provide preliminary evidence for the feasibility of extending the NOMV approach to other Gram negative bacteria.

What is claimed is:

1. An immunogenic composition for imparting an immune response to *Neisseria meningitidis* comprising native outer membrane vesicles having outer membrane proteins (OMPS) and lipopolysaccharides (LPS) obtained from *Neisseria meningitidis*, wherein said Neisseria is genetically altered so that the altered *Neisseria meningitidis* is unable to synthesize sialic acid.

2. The immunogenic composition of claim 1 wherein said Neisseria is genetically altered to increase immunogenicity of said native outer membrane vesicle by increasing expression of at least one antigen chosen from the group consisting of: PorA, PorB, Opc, transferrin binding protein, and lactoferrin binding protein.

3. The immunogenic composition of claim 1 wherein said Neisseria is genetically altered to reduce the toxicity of said native outer membrane vesicle.

4. The immunogenic composition of claim 3 wherein, said Neisseria is genetically altered to result in reduced expression of at least one antigen chosen from the group consisting of: reduction modifiable protein, htrB gene product, lipid A production, and LPS of the Lacto-N-neotetraose group.

5. A method for eliciting in an individual a mucosal immune reaction against Neisseria comprising mucosally administering a native lipopolysaccharide-containing outer membrane vesicle having outer membrane proteins (OMPS) and lipopolysaccharides (LPS) obtained from *Neisseria meningitidis*, which is genetically altered so that the altered *Neisseria meningitidis* is unable to synthesize sialic acid.

6. The purified native outer membrane vesicles composition of claim 1 wherein said *N. meningitides* is altered to express iron uptake proteins.

7. A mucosal vaccine against *N. meningiditis* infection comprising the composition of claim 1.

8. A mucosal vaccine against *N. meningiditis* infection comprising the composition of claim 2.

9. A mucosal vaccine against *N. meningiditis* infection comprising the composition of claim 3.

10. A mucosal vaccine against *N. meningiditis* infection comprising the composition of claim 4.

11. The method according to claim 5 wherein said mucosal administration is by a spray or swab.

12. The immunogenic composition according to claim 1 wherein the LPS and protein in the outer membrane are present in a ratio between about 0.2 to about 0.8.

13. The method according to claim 5 wherein the LPS and protein in the outer membrane are present in a ratio between about 0.2 to about 0.8.

14. The immunogenic composition according to claim 1 wherein the Neisseria has been cultivated under iron limiting conditions.

15. The method according to claim 5 wherein the Neisseria has been cultivated under iron limiting conditions.

16. The immunogenic composition according to claim 1 wherein the LPS and protein in the outer membrane are present in a ratio of about 0.2.

17. The method according to claim 5 wherein the LPS and protein in the outer membrane are present in a ratio of about 0.2.

* * * * *